United States Patent
Thornell et al.

(10) Patent No.: US 10,024,804 B2
(45) Date of Patent: *Jul. 17, 2018

(54) SYSTEM AND METHOD OF CHARACTERIZING MICRO-FABRICATION PROCESSES

(71) Applicant: Rudolph Technologies, Inc., Wilmington, MA (US)

(72) Inventors: John Thornell, Richardson, TX (US); Steven Knauber, Richardson, TX (US); Jatinder Dhaliwal, Plano, TX (US); Justin Miller, Bloomington, MN (US); Michael Grant, Minneapolis, MN (US); Kenneth Durden, Vadnais Heights, MN (US)

(73) Assignee: Rudolph Technologies, Inc., Wilmington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/601,239

(22) Filed: May 22, 2017

(65) Prior Publication Data

US 2017/0254757 A1 Sep. 7, 2017

Related U.S. Application Data

(63) Continuation of application No. 14/213,451, filed on Mar. 14, 2014, now Pat. No. 9,658,169.
(Continued)

(51) Int. Cl.
*G01N 21/88* (2006.01)

(52) U.S. Cl.
CPC ......... *G01N 21/8803* (2013.01); *G01N 21/88* (2013.01)

(58) Field of Classification Search
CPC combination set(s) only.
See application file for complete search history.

(56) References Cited

U.S. PATENT DOCUMENTS

| 4,618,938 A | 10/1986 | Sandland et al. |
| 4,644,172 A | 2/1987 | Sandland et al. |
| (Continued) | | |

FOREIGN PATENT DOCUMENTS

| DE | 69800756 T2 | 8/2001 |
| DE | 10131665 A1 | 1/2003 |
| (Continued) | | |

OTHER PUBLICATIONS

Hunt, Martin A., Karnowski, Thomas P., Kiest, Cary and Villalobos, Leda, "Optimizing Automatic Defect Classification Feature and Classifier Performance for Post-Fab Yield Analysis", 2000 IEEE/SEMI Advanced Semiconductor Manufacturing Conference, Copyright 2000, pp. 116-123.

(Continued)

*Primary Examiner* — Janese Duley
(74) *Attorney, Agent, or Firm* — Dicke, Billig & Czaja, PLLC

(57) ABSTRACT

A system for assessing a structure and the tools and processes used to form the structure is described. 2D images of the structure are captured and processed to obtain 3D information concerning the structure. Both 2D and 3D information is then used to identify and analyze selected characteristics of the structure. This analysis allows for a quality assessment of the structure. The selected characteristics are correlated with information relating to the operation of the tool that carried out the process that at least in part created the structure. The correlation of tool/process infor- (Continued)

mation to structure characteristics allows for the generation of feedback that may be used to modify the tool or processed used to form the structure.

12 Claims, 5 Drawing Sheets

Related U.S. Application Data

(60) Provisional application No. 61/800,331, filed on Mar. 15, 2013.

(56) References Cited

U.S. PATENT DOCUMENTS

| | | | |
|---|---|---|---|
| 5,592,295 | A | 1/1997 | Stanton et al. |
| 6,194,701 | B1 | 2/2001 | Task et al. |
| 6,215,897 | B1 | 4/2001 | Beer et al. |
| 6,248,988 | B1 * | 6/2001 | Krantz ................ G02B 21/004 250/201.3 |
| 6,597,802 | B1 * | 7/2003 | Bolle ................ G06K 9/00026 382/124 |
| 6,804,385 | B2 | 10/2004 | Eisfeld et al. |
| 6,947,588 | B2 | 9/2005 | Sim |
| 7,001,693 | B2 | 2/2006 | Liebmann et al. |
| 7,084,910 | B2 | 8/2006 | Amerson et al. |
| 7,092,557 | B2 | 8/2006 | Eisfeld et al. |
| 7,149,341 | B2 | 12/2006 | Hayashi et al. |
| 7,170,075 | B2 | 1/2007 | Oberski et al. |
| 7,248,282 | B2 | 7/2007 | Maddison |
| 7,616,804 | B2 | 11/2009 | Pai et al. |
| 7,634,129 | B2 * | 12/2009 | Strom .................. G06T 1/0007 345/419 |
| 7,813,832 | B2 | 10/2010 | Sundar |
| 8,072,503 | B2 | 12/2011 | Tischer |
| 8,218,840 | B2 | 7/2012 | Eisfeld et al. |
| 8,426,223 | B2 | 4/2013 | Voges et al. |
| 9,062,859 | B2 | 6/2015 | Voges et al. |
| 2001/0053557 | A1 | 12/2001 | Park |
| 2002/0054291 | A1 | 5/2002 | Tsai et al. |
| 2003/0169916 | A1 | 9/2003 | Hayashi et al. |
| 2004/0002154 | A1 | 1/2004 | Palsson |
| 2004/0113939 | A1 | 6/2004 | Zacks et al. |
| 2005/0013474 | A1 | 1/2005 | Sim |
| 2005/0036671 | A1 | 2/2005 | Watkins et al. |
| 2006/0109343 | A1 | 5/2006 | Watanabe et al. |
| 2006/0142971 | A1 * | 6/2006 | Reich ................ G01C 17/00 702/150 |
| 2006/0167583 | A1 | 7/2006 | Sundar |
| 2006/0251314 | A1 | 11/2006 | Eisfeld et al. |
| 2007/0057164 | A1 | 3/2007 | Vaughnn et al. |
| 2007/0237514 | A1 | 10/2007 | Pillman et al. |
| 2007/0258085 | A1 | 11/2007 | Robbins et al. |
| 2007/0269100 | A1 | 11/2007 | Higashi et al. |
| 2007/0286473 | A1 | 12/2007 | Leslie et al. |
| 2008/0013822 | A1 * | 1/2008 | Pai ..................... G01N 21/9501 382/145 |
| 2008/0212084 | A1 | 9/2008 | Watkins et al. |
| 2008/0232672 | A1 | 9/2008 | Birkner et al. |
| 2009/0161094 | A1 | 6/2009 | Watkins |
| 2009/0195786 | A1 | 8/2009 | Gastaldo |
| 2009/0196489 | A1 | 8/2009 | Le |
| 2011/0054659 | A1 | 3/2011 | Carlson et al. |
| 2011/0141267 | A1 | 6/2011 | Lev et al. |
| 2014/0287451 | A1 * | 9/2014 | McFetridge ............ C12M 1/18 435/29 |

FOREIGN PATENT DOCUMENTS

| | | |
|---|---|---|
| JP | 11281337 A | 10/1999 |
| KR | 20010044250 A | 6/2001 |
| WO | 00/04488 A1 | 1/2000 |
| WO | 02/059960 A1 | 8/2002 |

OTHER PUBLICATIONS

Patek, D.R., Tobin, K.W. and Jachter, L., "Machine Vision Inspection of Technical Ceramics", SPIE Digital Library, Feb. 21, 1996, pp. 253-257, vol. 2665.

Taiwanese Office Action for Taiwan Application No. 098130087, dated Nov. 26, 2014, 4 pgs.

* cited by examiner

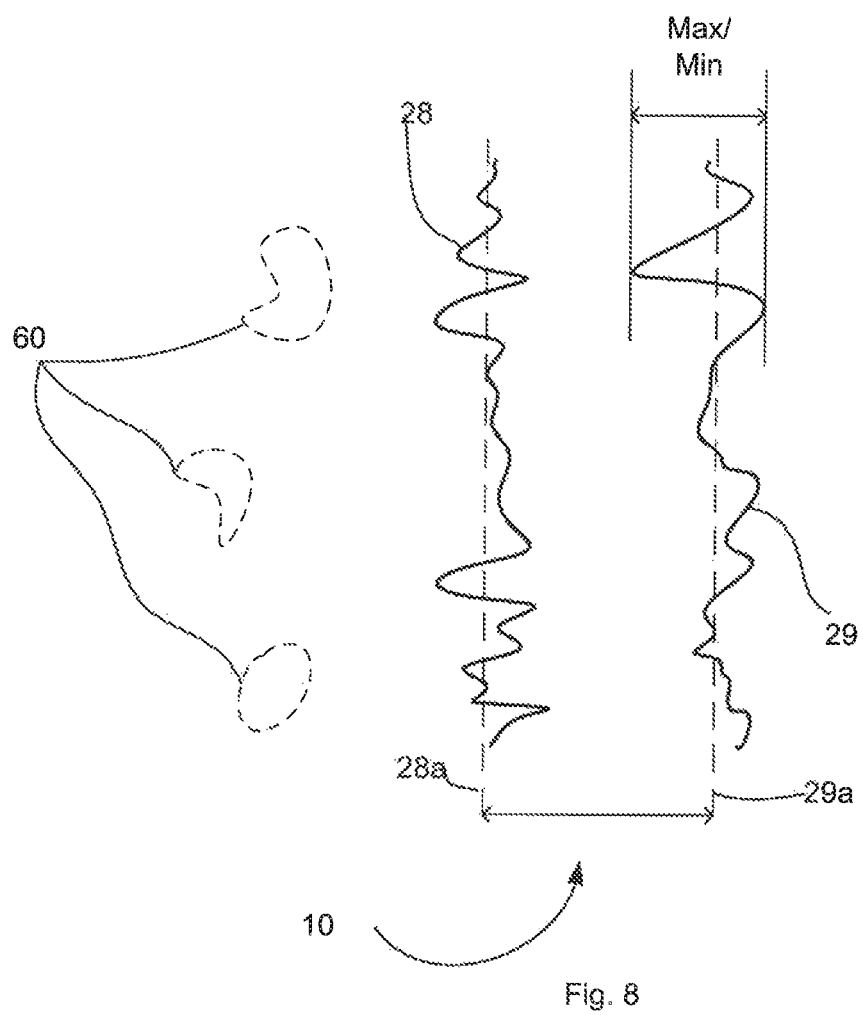

SYSTEM AND METHOD OF CHARACTERIZING MICRO-FABRICATION PROCESSES

CROSS-REFERENCE TO RELATED APPLICATION

This application is a continuation of U.S. patent application Ser. No. 14/213,451, filed Mar. 14, 2014 which claims the benefit of U.S. Provisional Application Ser. No. 61/800,331, filed Mar. 15, 2013, which is hereby incorporated by reference herein.

TECHNICAL FIELD

The present disclosure relates generally to assessment of microstructures formed using any of a number of microfabrication processes. More specifically, the present disclosure relates to systems and methods of observing structures created using microfabrication techniques and generating information useful for characterizing whether or how well the microfabrication techniques performed.

BACKGROUND

Optical techniques for observing substrate characteristics resulting from microfabrication processes such as thermal oxidation processes, chemical and physical vapor deposition processes of various kinds, epitaxy, photolithography and masking of various kinds, dry and wet etching processes of various kinds, laser ablation, focused ion beam milling and other similar techniques that are used to create or modify structures having features with critical dimensions on the order of a few micrometers or nanometers tend to be rather inflexible. Non-imaging techniques such as ellipsometry, scatterometry, and reflectometry permit the assessment of substrate or sample characteristics on a very small scale. However these techniques are generally useful only for the assessment of characteristics below a certain size or dimension, e.g. layer thicknesses on the order of a 10's or 100's of nanometers, structural features of a size that is on the order of the wavelength of light used to assess the structures and which generally are repetitive in nature or for particles that of a generally known type. These techniques are data intensive and require a large investment in mathematical models of specific structures and the hardware that can rapidly manipulate such models. Other non-imaging techniques such as laser triangulation are capable of locating small structures of a substrate when used as a scatterometer, but tend to be most useful for larger structures having dimensions that are larger than the wavelength of light being used for sensing purposes. The small spot size of a laser triangulation system allows one to build up a geometry of a structure that is assessed only on a point by point basis. Geometries of structures that interfere with the reflection of a fine beam (spot or line) of light become difficult to assess using this technique. Imaging techniques for assessing structures are limited to the native resolution of the optical system used to capture an image and also by the fact that the higher the resolution of the optical system, the more difficult it becomes to capture an image of an object that has a three-dimensional structure; the depth of focus of a higher resolution optical system limits the amount of a 3D structure that can be captured with the requisite focus needed to resolve structures of the object that fall outside the region that is in good focus. Accordingly, it is desirable to provide an approach to characterizing microfabrication processes in an accurate and efficient manner.

SUMMARY

Captured information is used to identify and analyze selected characteristics of a structure. This analysis allows for a quality assessment of the structure. The selected characteristics are correlated with information relating to the operation of a tool that carried out a process that at least in part created the structure. The correlation of tool/process information to structure characteristics allows for the generation of feedback that may be used to modify the tool or processed used to form the structure.

The system has a controller that is coupled to the imaging system and to the mechatronic support for coordinating their operation. The controller also receives images from the imaging system and is provided with software instructions for forming a concatenated image from the received images. The controller, or another computer of a similar type is provided with software instructions for identifying features of the structure in the concatenated image that are indicative of the operation of a microfabrication tool. The controller determines characteristics of the structure from the concatenated image such as roughness, inclination, skew, pitch, height, aspect ratio, presence/absence of discontinuities and sizes.

BRIEF DESCRIPTION OF THE DRAWINGS

FIG. 1 includes both a plan and a cross-section view of the structure.

FIG. 8 illustrates one embodiment of an assessment of a substrate.

DETAILED DESCRIPTION

Figure 1:
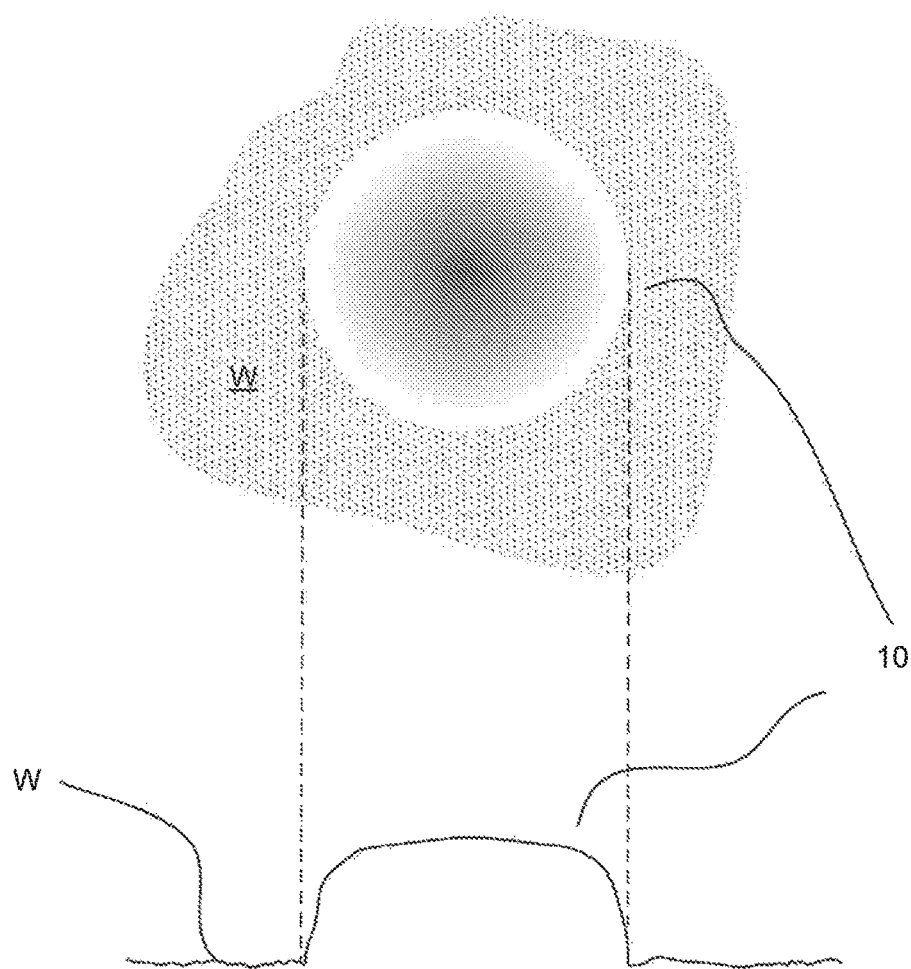
FIG. 1 is a schematic representation of an exemplary structure formed using a micro-fabrication technique.

In the following detailed description, reference is made to the accompanying drawings that form a part hereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims and equivalents thereof.

FIG. 1 is an illustration of a structure that may be assessed according to various embodiments of the concepts presented herein. The structure 10 is in this instance a generally cylindrical pillar that has been etched into a silicon wafer W. The exact method whereby the structure 10 was created is not critical to the present concepts, but may inform certain aspects of how the concepts are to be carried out. For example, where the structure 10 is created by means of laser ablation, not only might one be interested in measuring the geometry of the structure 10, but an inspection of the surface of the structure 10 and its surrounding area for damage and/or debris resulting from the micro-fabrication process used to create the structure may be desirable.

Figure 6:
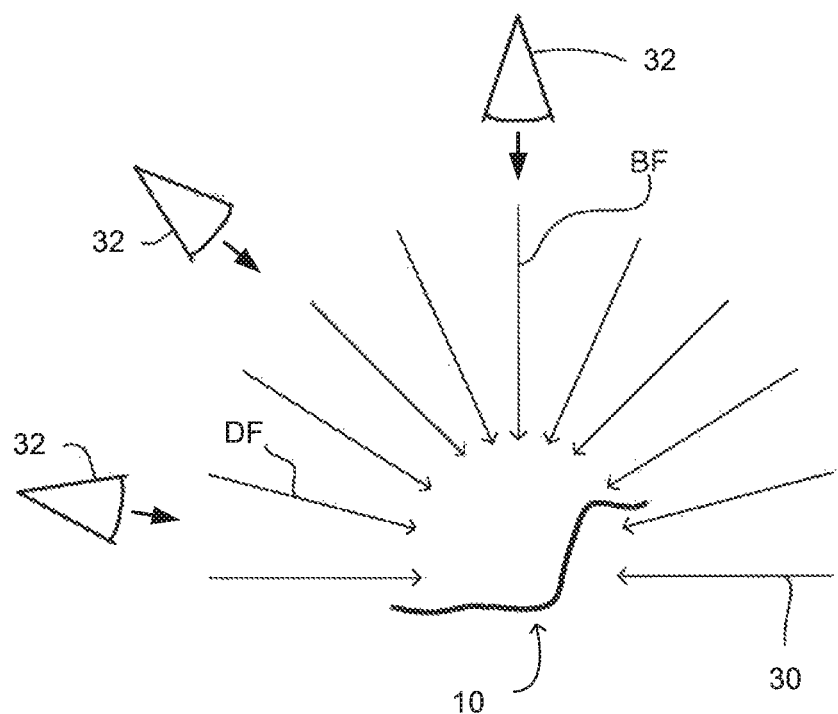
FIG. 6 is a schematic representation of illumination and imaging schemas that may be useful for imaging a structure.

As those skilled in the art are aware, an optical imaging system which includes an imaging device such as a CMOS or CCD camera chip also typically includes one or more optical elements for magnifying and/or focusing the object. An object is said to be in focus when the physical location of the object being imaged is within the field of view of the camera and also within its depth of field. In this way, an image having a specified resolution may be obtained. This generic set of optical conditions being met, an optical system can be arranged in many ways to obtain useful images of an object. FIG. 6 illustrates a number of possible arrangements for an imaging system according to the present invention. As can be seen, illumination light (arrows 30) is incident upon the structure 10. Note that illumination may be from a single direction or from multiple, simultaneous directions. Illumination may also be of any suitable wavelength or groups of wavelengths (i.e. broadband), the wavelength being selected using suitable a wavelength filter(s), single wavelength sources such as lasers of various types or a monochromator, for example. Similarly, illumination light 30 may be polarized in any useful fashion or unpolarized. Finally, illumination light 30 may be well collimated, uncollimated, convergent, or divergent. In short, it is desirable to use that type (angle of incidence, azimuth, intensity, wavelength, polarization, etc.) of illumination that will provide a requisite level of contrast in a resulting image. As seen in FIG. 6, the illumination light 30 that is normal to the object and which shares an optical axis with a camera 32 is commonly referred to as brightfield illumination. Illumination light 30 that does not share an optical axis with a camera 32 such as that labeled "DF" is commonly referred to as darkfield illumination. A combination of both brightfield and darkfield illumination can be useful in certain circumstances. In other instances, illumination light that is close to but not coincident with the optical axis of the camera 32 positioned directly above the structure 10 may be useful. This illumination is sometimes referred to as "greyfield" illumination as it approximates a combination of both bright field and darkfield illumination.

While the camera 32 positioned directly above structure 10 is commonly used as part of machine vision systems based on a standard microscope design, other arrangements may be used as well as represented by cameras 32 inclined with respect to the structure 10.

Figure 2:
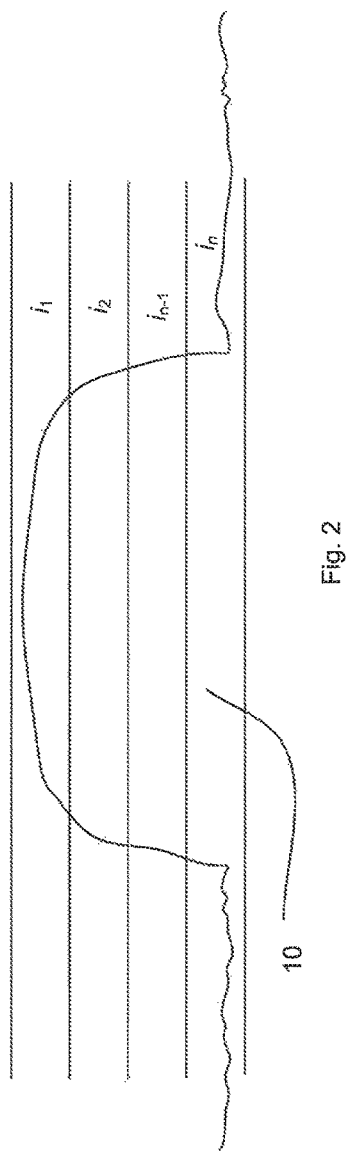
FIG. 2 is a schematic illustrating a scan of the depth of field of an imaging system through the height of the structure of FIG. 1.
Figure 3:
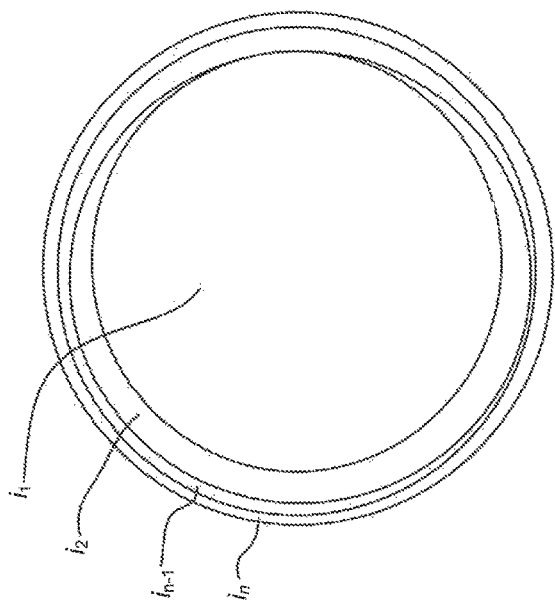
FIG. 3 is a schematic representation of the portions of the respective images of the structure that are in focus for a given field of view position.

Referring now to FIG. 2, it can be seen that the depth of field of an imaging system, particularly a high resolution imaging system, may not encompass the entirety of a structure 10 that is to be imaged. Where an imaging system is focused at the upper surface of the structure 10 by adjusting the imaging system to position the depth of field of the imager at the top surface, only that portion of the structure 10 encompassed by position $I_1$ will be in focus. To be certain, some light from the remainder of the structure 10 and from the background will be included in the image, but because those portions are out of focus, this light does not form a useful portion of the image. However it has been found that by bracketing substantially the entire structure 10 in successive images as by positioning the depth of field (focal plane) of an imaging system at successive positions $I_1$, $I_2$, ..., $I_{n-1}$, $I_n$, one may capture substantially the entire structure 10 in focus. The successive images are then processed together to identify those portions of each image that are in focus. The in-focus portions are then concatenated to form a single composite image of the structure 10 in which the entire image is in focus. One manner in which the in-focus portions of each of the successive images are identified is by determined which pixels in an image are brightest. FIG. 3 illustrates schematically how portions $i_1$ to $i_n$ of the concatenated image are assembled to form an entire composite/concatenated image of the structure 10. Each part or pixel of the concatenated image represents a specific X,Y position on the structure 10. Height or Z information may be obtained, with an error related to the size of the depth of field of the imaging system, by noting the position of the depth of field of from which the in-focus pixels were obtained.

Once a concatenated image 12 is obtained, inspection of the substrate and/or assessment of microfabrication tool operation may take place. In one embodiment the image 12 may be compared to a pre-defined model and in other embodiments features present in the image may be identified and characteristics thereof may be determined and recorded. In both cases, the results of the comparison/analysis may be acted upon immediately or on a delayed basis.

One type of model that may be used is a statistical model in which multiple images of the structure under test are captured and analyzed to produce a model of what an ideal structure should look like in an image 12. This type of model allows for a pixel by pixel comparison of the model and images 12. In one example the model is defined as an array of pixel value ranges, one range for each pixel in the model. Where a pixel in an image 12 falls outside of the range of values established for that pixel in the model, the pixel of the image 12 is noted as potentially being discrepant. Depending on the nature of the assessment, a single discrepant pixel may be sufficient to categorize the structure or the microfabrication tool used to at least partially form it as out of specification. In the case of a semiconductor device having a discrepant structure this may mean that the device is discarded or that it is diverted for some type of re-work. In the case of microfabrication tools, the presence of one or more discrepant pixels in an image 12 may be used to modify the operation of one or more of the microfabrication tools used to form the structure.

In some embodiments a model can be purely statistically derived such as by defining a "golden value" for each pixel as a mean of corresponding pixels from multiple concatenated images 12. While a direct comparison may be useful in some instances, it is typically more desirable to assess a degree of difference between a golden value and an actual value. Accordingly, a range such as that described above may be developed statistically by generating a standard deviation for a given pixel and using that as a range. However it has been found that applying an heuristic modification to statistically derived ranges to achieve better results. A suitable heuristic may involve simply narrowing or expanding a range to decrease or increase sensitivity of the assessment algorithm. One alternative to an heuristic would be to use neural network modeling to identify an appropriate adjustment to a model's range of acceptable values based on outcomes, i.e. quality, of the structures being fabricated and assessed.

Figure 5:
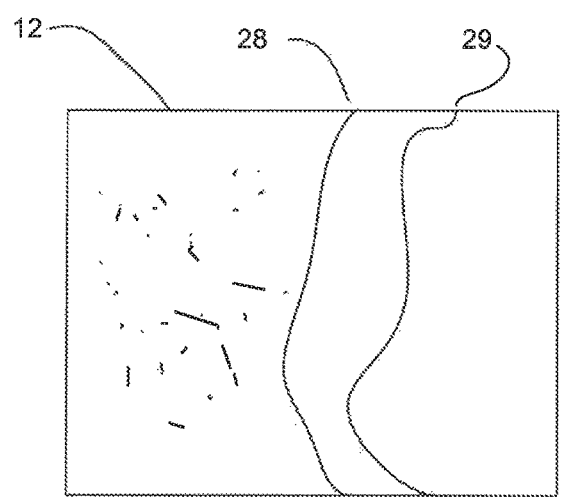
FIG. 5 is a representation of a two dimensional image resulting from the concatenation of the in-focus portions shown in FIG. 3.

In some instances, such as where inherent variability reduces the utility of a pixel based model, a structure under evaluation is imaged to form a concatenated image 12 which is then analyzed to identify and characterize features of the structure that appear in the image 12. In some cases an edge finding algorithm may be used to determine the presence and location of boundaries such as lower edge 28 and upper edge 29 (FIG. 5). Examples of suitable image processing algorithms include Canny and Sobel edge finding techniques. Other approaches may also be used. Similarly, characteristics such as surface roughness of a structure may be assessed by analyzing a concatenated image 12 by passing a kernel over the concatenated image to determine relative variability in intensity in the respective areas. For example, the standard deviation of pixel values (whatever the recorded value may be, e.g. intensity, hue, saturation, wavelength, polarization state), may be determined for each 2×2, 3×3, etc. sized region centered on each pixel or on a selected sub-set of pixels. Where standard deviation values vary beyond a given value that may be determined on the basis of correlation with past measurements, on an heuristic or on an arbitrary value, it can be said that a surface is rough and a quantization of that roughness may be computed, if so desired.

In other instances a concatenated image 12 may be assessed using techniques that are known as blob analysis. These image processing techniques are useful for identifying regions that have similar characteristics. In one embodiment, a concatenated image 12 is analyzed to identify all pixels or regions that have values (e.g. intensity) that are outside of a given range. Blob analysis software attempts to determine whether the identified pixels or regions are discrepant by themselves or are part of a larger region or structure that is itself discrepant. For example, if a given pixel has an intensity value that is higher than a given value, blob analysis may be used to determine if adjacent pixels or regions have a similar character. If so, the similar pixels or regions may be grouped together and identified as a single blob which may or may not (depending on assessment criteria) be discrepant.

Figure 4:
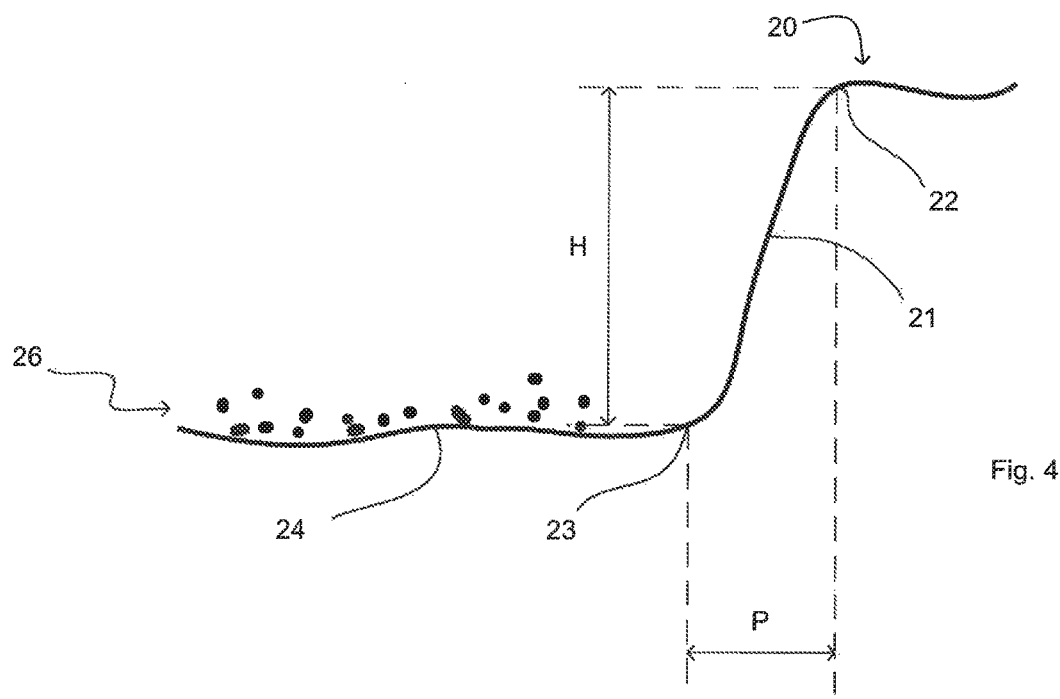
FIG. 4 is a cross-sectional representation of a portion of the structure of FIG. 1 showing an exemplary geometry thereof.

In addition to finding features on a structure, the present concepts may be used to characterize the geometry of a structure itself. As indicated above, one may be able to determine a surface roughness of a region 26 (FIG. 4) of a structure as represented in a concatenated image 12. Surface roughness may also be determined on the basis of height information obtained during the concatenation process. In one embodiment all height values for a given region are assessed to determine if they fall within a predetermined range which may be a statistical deviation, an heuristic value/range or a range arbitrarily determined by a designer of the structure that is under test, e.g. desired surface roughness specification.

Using the geometric location of edges 28, 29, one may also determine the pitch P of these edges, the difference in height/altitude H, and the slope 21 of the surface of the structure. The slope 21 may also be assessed using surface roughness or blob analysis techniques described above to obtain some value of variability for the surface.

Information about a structure and its characteristics can be correlated to and/or analyzed with additional process information to fully character the process used to form the structure. One very helpful analysis is to correlate operational data derived from microfabrication tools used to form a structure to particular characteristics of the structure itself. In one embodiment operational data from a microfabrication tool that etches or ablates a portion of a substrate to form a structure 10 is correlated with the geometry of the structure 10 itself. If a slope/sidewall 21 of the structure 10 is intended, for example, to be substantially vertical, one can measure the inclination of the slope 21 and correlate this inclination with, for example, a power output, temperature or dose/dwell time of the microfabrication tool. Understanding relationships like this can be helpful to an operator of a specific microfabrication tool and to the operator of a fabrication facility that encompasses an entire fabrication process.

Note that correlation of data concerning one or more microfabrication processes with structures 10 may take place in either or both real time or on a delayed basis. In a preferred embodiment, data concerning microfabrication processes is captured on an ongoing basis and information that can tie this data to one or more substrates/structures is similarly captured. For example, the operating characteristics of a microfabrication tool are recorded and appended to a database or other data structure with a cross-reference to the substrates/structures that were processed by the selected microfabrication tool. The characteristics of the structure 10 that are of interest or which are to be controlled are similarly recorded such that a connection between tool and structure can be made. Since the recordation of microfabrication tool data and structure characteristics tends to be linear, determination of good or bad function of a tool is made after a structure has been formed, this correlation is used to control the operation of a microfabrication tool as it processes subsequent substrates. In those situations where a structure may be assessed in more or less real time, e.g. deposition processes that may be measured on an ongoing basis, the control feedback loop may be made in more or less real time. It is to be understood however, that very often a time shifted correlation/control arrangement is determined before real time control of microfabrication tools may be accomplished.

Figure 7:
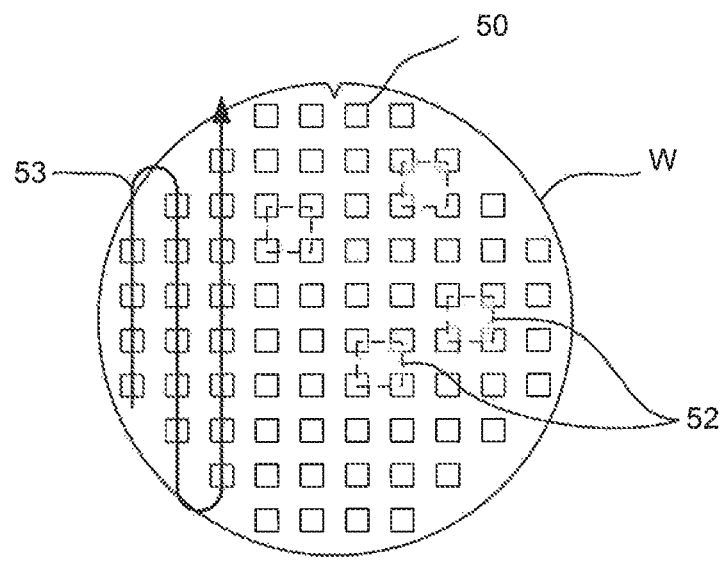
FIG. 7 is a representation of how assessment information may be obtained from a semiconductor wafer.

FIG. 7 illustrates examples of how images for deriving a concatenated image 12 may be obtained. In the illustrated example the substrate is a wafer W having a number of die 50 disposed thereon. Die 50 are typically formed in uniform arrays though other arrangements are possible. Since images at multiple focal positions are required to obtain a concatenated image 12, multiple images at each site where a structure 10 that is to be analyzed must be captured. Fields of view 52 are arranged to be coincident with structures 10. An imaging system consisting a camera, optics and illumination (not shown) is positioned at the selected fields of view 52 and images at discrete focal positions are captured. This may be referred to as "stop and scan" as the mechatronic support that moves the substrate stops to allow the imaging system to capture its images. Alternatively, a more continuous image collecting process may be undertaken as represented by arrow 53. Arrow 53 represents a boustrophedon path that addresses the imaging system (not shown) to each structure that is to be assessed without stopping. In this approach, the operation of the mechatronic support (stage) is coordinated with the imaging system to capture images of the structures at a single focal position. Note that where illumination is strobed, the strobe of the imaging system is correlated to the speed at which the mechatronic support moves. Linescan imaging systems, which do not strobe, may also be used. Subsequent scans of the substrate are made at different focal positions. The number of required scans is set to the number of different focal position images are required for the desired analysis of each structure. A higher resolution assessment of structures 10 may necessitate more images/passes and vice versa.

In another embodiment, an image of an entire substrate may be captured at one time. Typically this is done using optics that are scaled to the size of the substrate and which have a numerical aperture that defines a suitable depth of field to permit the formation of a concatenated image having a desired depth resolution as described above. Imaging is preferably conducted at normal incidence to the substrate and is undertaken at multiple focal positions. Illumination may be brightfield, darkfield, a combination of both and may also include other features as wavelength specific filtering and/or polarization of light.

FIG. 8 illustrates an embodiment of how the present invention may be used to assess the operation of a microfabrication tool that is used to form a structure 10. As can be seen, edges 28, 29 define a sidewall or slope of a structure 10. The position and nature of these edges is directly correlated to the function of a microfabrication tool that forms the structure 10. In one embodiment, edges 28, 29 would be uniformly straight and parallel to one another. In reality, these edges are rough and may not be parallel. Lines 28a and 29a are fit to the identified edges 28 and 29 using known line fitting techniques. The degree of parallelism (in the plane of the substrate, i.e. XY, and out of the plane of the substrate, i.e. XYZ) may be quantified as well as the distance between the two lines 28a, 29a. In addition, a variability or deviation of an edge such as edge 29 as compared to its line of best fit 29a may be quantified. A maximum and minimum deviation from a nominal position for an edge may be determined as well. The position of the maximum and minimum deviation may be compared directly to other information that is derived directly from the concatenated image 12 of the structure 10 or to a standard, range or specification of a type described above. The position or presence of additional features such as blobs 60 adjacent to one or both of the edges 28, 29 may also be indicative of microfabrication tool operation.

Conclusion

Although specific embodiments of the present invention have been illustrated and described herein, it will be appreciated by those of ordinary skill in the art that any arrangement that is calculated to achieve the same purpose may be substituted for the specific embodiments shown. Many adaptations of the invention will be apparent to those of ordinary skill in the art. Accordingly, this application is intended to cover any adaptations or variations of the invention. It is manifestly intended that this invention be limited only by the following claims and equivalents thereof.

What is claimed is:

1. A system for assessing structures formed by microfabrication processes and the microfabrication processes themselves comprising:
   an imaging system comprising a camera, optics and illumination for obtaining 2D images of a structure at multiple focal positions of the imaging system relative to the structure to substantially characterize both 2D and 3D geometries of the structure;
   a mechatronic support for moving the structure relative to the imaging system to address a field of view of the camera to the structure; and
   a controller coupled to the imaging system and to the mechatronic support for coordinating operation thereof and for receiving images from the imaging system, for identifying in focus portions of individual received images of the structure at multiple different focal positions of the imaging system relative to the structure, for forming a concatenated image from the in focus portions of the received images, each pixel of the concatenated image having an XY position identical to its XY position in the image from which it is derived and a Z position derived from the focal position of the image from which it is derived and for identifying features of the structure in the concatenated image that are indicative of the operation of a microfabrication tool.

2. The system of claim 1, wherein the controller is constructed and arranged to identify characteristics of the structure selected from a group consisting of: roughness, inclination, skew, pitch, height, aspect ratio, presence/absence of discontinuities, and size.

3. The system of claim 1, wherein the controller is further programmed to:
   generate a 2D model of the structure comprising at least a range of acceptable values for each pixel in the concatenated image; and
   compare a subsequent test image of a structure with the 2D model on a pixel by pixel basis to identify potentially discrepant portions of the structure in the test image.

4. The system of claim 1, wherein the controller is further programmed to:
   identify a 2D location of a feature of the structure in the concatenated image;
   determine a 3D characteristic of the feature of the structure using the X, Y and Z positions of the pixels that represent the feature of the structure; and
   assess the characteristic of the feature of the structure to determine whether the structure satisfies a predetermined criteria.

5. The system of claim 4, wherein the controller is further programmed to:
   identify a first edge and a second edge of the structure in the concatenated image;
   determine a 3D position of each of the first and second edges relative to one another; and
   assess whether the relative positions of the first and second edges satisfy a predetermined geometric criteria.

6. The system of claim 5, wherein the predetermined geometric criteria is selected from a group consisting of a vertical critical dimension, a horizontal critical dimension, a Euclidian distance, a pitch and a slope.

7. The system of claim 1, wherein the controller is further programmed to:
   identify an edge of the structure present in the concatenated image;
   determine a shape in 3D space of the edge of the structure; and
   assess a dimensional variability of the shape of the edge of the structure in at least one of XY, XZ, and YZ planes.

8. The system of claim 1, wherein the controller is further programmed to:
   identify a feature of interest and a fiducial feature of the structure present in the concatenated image;
   determine a shape and a position in 3D space of the feature of interest of the structure relative to the fiducial feature; and
   assess alignment of the feature of interest relative to the fiducial feature.

9. The system of claim 8, wherein the controller is further programmed to:
determine an alignment between the feature of interest and the fiducial feature in at least one of XY, XZ and YZ planes.

10. The system of claim 1, wherein the imaging system has a depth of field, and further wherein the Z position of each pixel of the concatenated image is derived from a position of the depth of field of the imaging system for the individual received image otherwise providing an in-focus pixel from which a corresponding pixel of the concatenated image is derived.

11. The system of claim 10, wherein the Z position of each pixel of the concatenated image is assigned an error related to a size of the depth of field of the imaging system.

12. The system of claim 1, wherein the imaging system is configured to provide greyfield illumination of the structure.

* * * * *